United States Patent [19]
Kuwata et al.

[11] Patent Number: 4,802,957
[45] Date of Patent: Feb. 7, 1989

[54] METHOD FOR MEASURING THE WATER CONTENT OF A SOLID SAMPLE USING KARL FISCHER'S COULOMETRIC TITRATION

[75] Inventors: Sinichi Kuwata, Machida; Hiromasa Katoh, Tama; Mitsumasa Ono, Ebina, all of Japan

[73] Assignee: Mitsubishi Chemical Industries Limited, Japan

[21] Appl. No.: 850,527

[22] Filed: Apr. 10, 1986

[30] Foreign Application Priority Data

Apr. 26, 1985 [JP] Japan .................. 60-90520

[51] Int. Cl.$^4$ ................. G01N 31/16; G01N 33/18
[52] U.S. Cl. ..................... 204/1 T; 436/42; 204/405
[58] Field of Search .............. 436/41, 39, 42; 204/1 T, 405

[56] References Cited

U.S. PATENT DOCUMENTS 4,354,853 10/1982 Dahms ................. 204/1 T
4,368,105 1/1983 Muroi et al. ........... 204/1 T
4,378,972 4/1983 Scholz ................. 436/42
4,619,900 10/1986 Scholz ................. 436/42

FOREIGN PATENT DOCUMENTS 0075246 3/1983 European Pat. Off. ...... 436/42
0004236 2/1970 Japan .................. 436/41
0018196 5/1972 Japan .................. 436/41
0015019 2/1980 Japan .................. 436/41
0027650 3/1981 Japan .................. 436/42
2069148 8/1981 United Kingdom .
2152676 8/1985 United Kingdom .

Primary Examiner—Barry S. Richman
Assistant Examiner—Robert J. Hill, Jr.
Attorney, Agent, or Firm—Jordan B. Bierman

[57] ABSTRACT

An electrolytic solution for Karl Fischer's coulometric titation and a method for measuring the water content of a sample using the same are disclosed. The electrolytic solution contains iodine or an iodide, sulfur dioxide, an amine and a solvent, wherein the amine is a pyridine derivative, imidazole or an imidazole derivative and the solvent is a mixture of (a) a polyhydric alcohol or an ether compound thereof, (b) methanol and (c) a halogenated hydrocarbon or an aromatic hydrocarbon. The measurement method achieves a high precision with reduced measurement time and is suitable for making water content measurements using a water content vaporization method.

4 Claims, 2 Drawing Sheets

METHOD FOR MEASURING THE WATER CONTENT OF A SOLID SAMPLE USING KARL FISCHER'S COULOMETRIC TITRATION

FIELD OF THE INVENTION

This invention relates to an electrolytic solution for Karl Fischer's coulometric titration and a method of measuring the water content of a sample using the same. More particularly, it relates to an electrolytic solution for Karl Fischer's coulometric titration which is suitable for measuring the water content of solid samples by a vaporization method, and to a method for measuring the water content of a solid sample.

BACKGROUND OF THE INVENTION

Measurement of the water content of a solution has conventionally been conducted by utilizing Karl Fischer's reaction, which was discovered by Karl Fischer. The conventionally employed electrolytic solution for Karl Fischer's coulometric titration generally comprises the following components (i) to (iv):
(i) Iodine or an iodide
(ii) Sulfur dioxide
(iii) Pyridine
(iv) Solvent The solvents for the electrolytic solution which have so far been employed include alcohols, e.g., methanol, ethanol, chloroform, propylene carbonate, and the like.

When using methanol as the solvent (iv), the reaction between the electrolytic solution for Karl Fischer's (hereinafter KF) coulometric titration and water proceeds as follows:

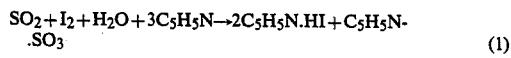
(1)

(2)

According to KF coulometric titration, iodine in the above-described formula (1) is internally formed by electrolytic oxidation of an iodide ion, and the thus formed iodine and water are allowed to react. The water content in a sample to be analyzed can be determined by the amount of iodine generated. More specifically, measurement of the water content of a sample can be carried out by charging the electrolytic solution (anolyte) in an anode chamber and an appropriate catholyte in a cathode chamber, passing an electric current therethrough to previously remove the water content of the anolyte, supplying a sample to be analyzed to the electrolyte, and again passing a current therethrough to titrate the water content of the sample. When using iodine in the preparation of the electrolytic solution, the above operation is followed, after water is added to the electrolytic solution, until the iodine color disappears.

In recent years, pyridine as the component (iii) has been replaced by imidazole as taught in Japanese Patent Application (OPI) No. 137250/81 (the term "OPI" herein used means "published unexamined application") due to the peculiar offensive smell of pyridine.

However, when these conventional electrolytic solutions are applied to measuring the water content of a solid sample, that is not dissolved in an electrolytic solution, by means of a water content vaporization apparatus, the solvent may vaporize during measurement to cause precipitation of a solid, thus giving rise to the following problems. That is, a commercially available KF coulometric titration apparatus and a commercially available water content-vaporization apparatus are connected, for example, as shown in FIG. 1. Electrolytic solution (anolyte) (18) is placed in an anode chamber of titration vessel (2) of KF coulometric titration apparatus (1), and an appropriate catholyte is placed in a cathode chamber, followed by passing an electric current therethrough to remove water in the anolyte. In the vaporization apparatus (4), the water content of a solid sample is vaporized according to an operating procedure for the apparatus. Specifically, a solid sample (8) is fed into boat (7) placed in heating tube (6) from sample feeder (10) through outlet (9), and the boat is then pushed into heating furnace (5) by pusher (11). The water content in the sample is vaporized by heating while controlling the temperature inside heating furnace (5) by means of temperature controller (15). The water vapor is driven out of the funnel together with carrier gas (19), e.g., nitrogen, which is introduced into heating furnace (5) through drying tubes (12) and (13) containing a desiccant, e.g., phosphorus pentoxide (16) or silica gel (17). The amount of the carrier gas to be introduced is controlled by means of flow meter (14). The water vapor is blown into electrolyte (18) in titration vessel (2) via blowing tube (3), wherein the water is titrated by means of coulometer (1).

In the above-described operation, the solvent in the electrolytic solution is vaporized away in the neighborhood of the blowing tube during the water content measurement. As a result, oil droplets or a solid precipitate is attached to the inner wall of the blowing tube connecting the vaporization apparatus and the titration vessel, and the water from the sample is adsorbed thereon, which results in a tendency to lower the water content measured. Even if the adsorbed water is desorbed, desorption not only takes time but also fails to assure accuracy of the measurement and, in addition, deteriorates reproducibility.

SUMMARY OF THE INVENTION

Accordingly, an object of this invention is to eliminate the above-described problems and to provide a non-pyridine type electrolytic solution for KF coulometric titration, with which the water content of a solid sample can be measured by a water vaporization method with high accuracy and also which can be utilized in a wide application.

Another object of this invention is to provide a KF coulometric titration method which is suitable for measurement of the water content of a solid sample in the form of water vapor.

The present invention relates to an electrolytic solution for KF coulometric titration, comprising iodine or an iodine, sulfur dioxide, an amine and a solvent, wherein said amine is a pyridine derivative, imidazole or an imidazole derivative, and said solvent is a mixture of (a) a polyhydric alcohol or an ether compound thereof, (b) methanol and (c) a halogenated hydrocarbon or an aromatic hydrocarbon; and to a method of measuring the water content of a solid sample by KF coulometric titration with an electrolytic solution of KF coulometric titration comprising iodine or an iodide, sulfur dioxide, an amine and a solvent, wherein said amine is a pyridine derivative, imidazole or an imidazole derivative, and said solvent is a mixture of (a) a polyhydric alcohol or an ether compound thereof, (b) methanol and (c) a halogenated hydrocarbon or an aromatic hydrocarbon.

BRIEF DESCRIPTION OF THE ACCOMPANYING DRAWINGS

FIG. 1 shows an apparatus for KF coulometric titration by a water vaporization method, which can be used in the present invention.

FIGS. 2 to 5 are titration curves, in which the time is plotted as abscissa and the electrolytic current as the ordinate. The time axis in FIGS. 4 and 5 is scaled down to half that of FIGS. 2 and 3. In each of FIGS. 2 to 5, point E indicates the titration end-point, and the arrow indicates the point at which an electrolytic solution is made to flow backward to a blowing tube and then again made to flow forward.

DETAILED DESCRIPTION OF THE INVENTION

Figure 1:
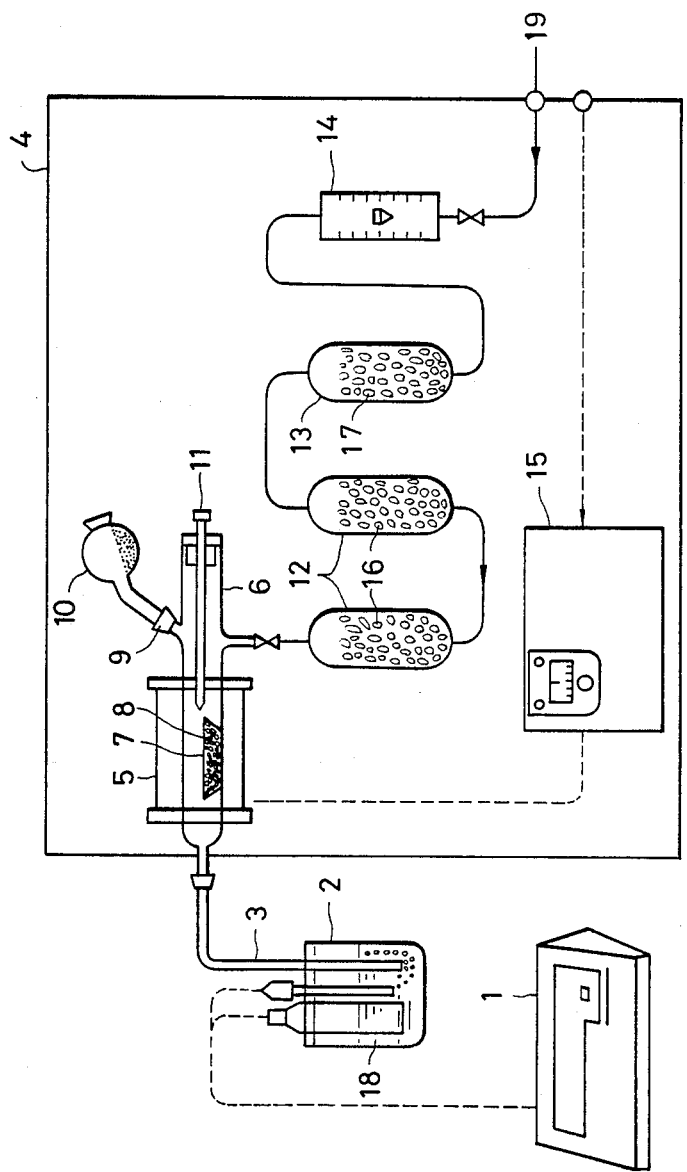

The electrolytic solution which can be used in the present invention comprises iodine or an iodide, sulfur dioxide, a specific amine and a specific solvent.

The iodide to be used preferably includes hydroiodic acid, potassium iodide, sodium iodide, etc.

The iodine or iodide content in the electrolytic solution usually ranges from 3 to 0.1% by weight, and preferably from 2 to 0.3% by weight in the form of iodine.

The concentration of sulfur dioxide in the electrolytic solution as well as the basicity of the amine (hereinafter described) greatly influence the reaction rate. For example, even when an amine having low basicity is used, the reaction rate can be increased by increasing the concentration of sulfur dioxide. The sulfur dioxide content in the electrolytic solution usually ranges from 0.3 to 12% by weight, and preferably from 1.2 to 6% by weight, with its weight ratio to the amine being in the range of from 0.2:1 to 3.3:1.

The amine which can be used in the present invention is selected from a pyridine derivative, imidazole and an imidazole derivative. The pyridine derivative includes 4-dimethylaminopyridine, 1,3-di-(2-pyridyl)propane, 1,3-di-(4-pyridyl)propane, and the like. The imidazole derivative includes 1-methylimidazole, 2-ethylimidazole, 2-phenylimidazole, and the like.

The above-described amine is used in the electrolytic solution usually in an amount of from 3 to 30% by weight, and preferably from 5 to 20% by weight.

The polyhydric alcohol of solvent component (a) includes those having from 2 to 4 carbon atoms and 2 or 3 hydroxyl groups, such as ethylene glycol, propylene glycol, 1,3-butylene glycol, 1,4-butylene glycol, glycerin, etc.; and condensates of polyhydric alcohols, such as polyethylene glycol, polypropylene glycol, etc.

The ether compounds of polyhyric alcohols which are also used as solvent component (a) include alkyl ethers of the above-mentioned polyhydric alcohols such as ethylene glycol monomethyl ether, ethylene glycol monoethyl ether, ethylene glycol monobutyl ether, 1-methoxy-2-propanol, and the like.

The polyhydric alcohol or its ether to be used generally has a purity of 95% or higher, and is usually used in an amount of from 3 to 30% by volume, and preferably from 5 to 20% by volume, based on the electrolytic solution.

The methanol of solvent component (b) is used usually in a mixing ratio to the polyhydric alcohol or its ether of from 0.1:1 to 15:1, preferably from 1:1 to 8:1, and more preferably from 2:1 to 5:1, in terms of volumetric ratio at room temperature.

The halogenated hydrocarbon of solvent component (c) includes chloroform, 1,1,1-trichloroethane, etc., and the aromatic hydrocarbon includes xylene, toluene, etc. The halogenated hydrocarbon or aromatic hydrocarbon exhibits a high dissolving power for various substances and also accelerates the Karl Fischer's reaction.

The content of the halogenated hydrocarbon or aromatic hydrocarbon in the electrolytic solution usually ranges from 5 to 60% by weight, and preferably from 10 to 50% by weight.

Measurement of the water content of a solid sample by the use of the above-described electrolytic solution can be carried out in a known manner as described above with reference to FIG. 1. The catholyte to be used is not particularly limited as long as it induces an electrochemical counter reaction when electricity is carried between two electrolytes. A typical catholyte is a mixture comprising 65% by weight of methanol, 20% by weight of carbon tetrachloride, 5% by weight of sulfur dioxide and 10% by weight of 4-dimethylaminopyridine.

The electrolytic solution in accordance with the present invention can be applied to measuring the water content of various substances, preferably including various solid substances such as inorganic compounds, ceramics, agricultural chemicals, pharmaceuticals, plastics, and the like. The method according to the present invention makes it possible to measure the water content of the aforesaid various solid substances with high precision.

This invention will now be illustrated in greater detail with reference to the following examples, but it should be understood that they are not intended to limit the present invention.

EXAMPLE 1

27.2 g of imidazole, 2.54 g of iodine, 12.8 g of sulfur dioxide, 30 ml of ethylene glycol and 50 ml of chloroform were dissolved in methanol to prepare 200 ml of an electrolytic solution. The resulting electrolytic solution was charged into the anode chamber of a commercially available Karl Fisher coulometric titration apparatus (Mitsubishi Moisture Meter Model "CA-02", manufactured by Mitsubishi Chemical Industries, Ltd.). On the other hand, a mixture comprising 65% by weight of methanol, 20% by weight of carbon tetrachloride, 5% by weight of sulfur dioxide and 10% by weight of 4-dimethylaminopyridine was put in the cathode chamber.

Figure 3:
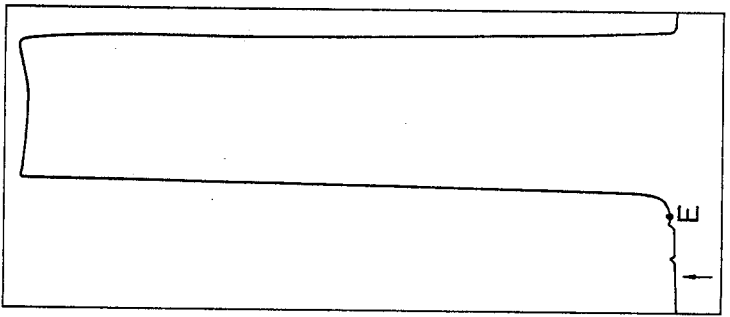

In order to vaporize the water content of the solid sample and blow the water vapor into the anolyte, a commercially available vaporization apparatus (Water Vaporizer Model "VA-02", manufactured by Mitsubishi Chemical Industries, Ltd.) was connected to the titration apparatus as shown in FIG. 1. The vaporization apparatus was set at 150° C., and nitrogen gas was fed as a carrier gas at a rate of 250 ml/min. Water was added to the anolyte until the iodine color disappeared. An electric current was passed between the anolyte and the catholyte to remove any water content in the anolyte. Then, 10 $\mu$l of water was put in a boat of the vaporization apparatus by the use of a micro syringe, vaporized, driven out of the vaporization apparatus together with the carrier gas and blown into the electrolytic solution in a titration vessel through a blowing tube. The water content in the electrolytic solution was measured according to the operation procedure of the titration apparatus to obtain the titration curve and analysis values as shown in FIG. 3 and Table 1, respectively.

EXAMPLE 2

The procedure of Example 1 was repeated except for using 10 ml of propylene glycol in place of ethylene glycol. The titration curve and analysis values obtained were the same as obtained in Example 1.

EXAMPLE 3

The procedure of Example 1 was repeated except for using 30 ml of ethylene glycol monobutyl ether in place of ethylene glycol. The titration curve and analysis values obtained were the same as obtained in Example 1.

EXAMPLE 4

The procedure of Example 1 was repeated except for using 30 ml of polyethylene glycol (average molecular weight: 200) in place of ethylene glycol. As a result, the titration curve and analysis values obtained were the same as in Example 1.

EXAMPLE 5

Figure 5:
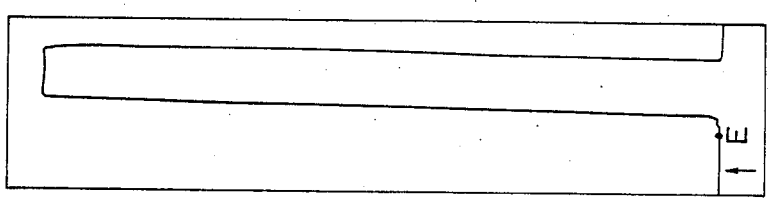

An electrolytic solution was prepared by adding 20 ml of propylene glycol to a solution consisting of 31.8 g of imidazole, 2.58 g of iodine, 12.3 g of sulfur dioxide, 40 ml of chloroform and 108 ml of methanol. Each of 10 μl of water and 30 μl of a water/methanol standard solution (about 20 mg-H₂O/ml) was measured for its water content in the same manner as described in Example 1 but using the above prepared electrolytic solution. The titration curve for 10 μl of water is shown in FIG. 5, and the analysis values for the water sample and water/methanol sample are shown in Tables 1 and 2, respectively.

COMPARATIVE EXAMPLE 1

Figure 2:
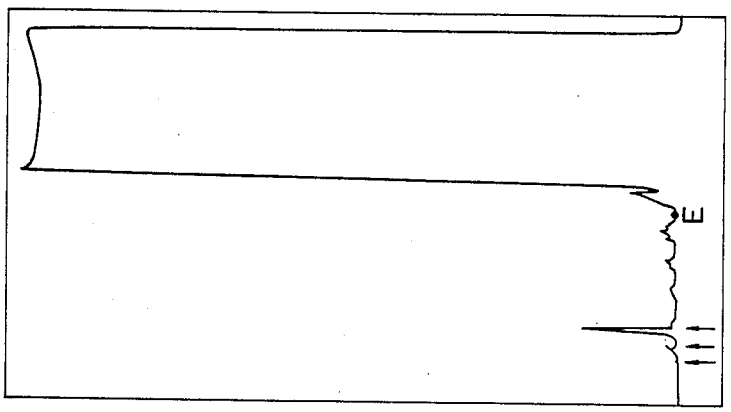

27.2 g of imidazole, 2.54 g of iodine, 12.8 g of sulfur dioxide and 50 ml of chloroform were dissolved in methanol to prepare 200 ml of an electrolytic solution. Using this electrolytic solution, 10 μl of water was subjected to measurement in the same manner as in Example 1. The titration curve and analysis values obtained are shown in FIG. 2 and Table 1, respectively.

COMPARATIVE EXAMPLE 2

Figure 4:
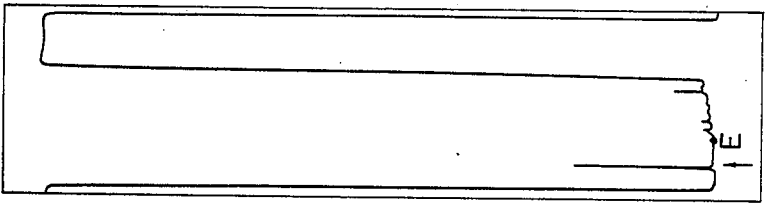

An electrolytic solution (200 ml) was prepared from 35.4 g of imidazole, 2.88 g of iodine, 13.6 g of sulfur dioxide, 45 ml of chloroform and 120 ml of methanol. Water content measurements were conducted in the same manner as described in Example 5 but using the above prepared electrolytic solution. The titration curve for the water sample is shown in FIG. 4, and the analysis values obtained for the water sample and the water/methanol sample are shown in Tables 1 and 2, respectively.

TABLE 1

|  | Example 1 | Example 5 | Comparative Example 1 | Comparative Example 2 |
|---|---|---|---|---|
| Measured Value for 10.0 mg of water (mg) | 10.027 | 10.061 | 9.977 | 9.962 |
|  | 10.036 | 10.039 | 9.924 | 10.013 |
|  | 10.032 | 10.092 | 9.961 | 10.038 |
|  | 10.018 |  | 9.977 |  |
|  | 10.030 |  | 9.988 |  |
| Averaged Value (mg) | 10.029 | 10.064 | 9.965 | 10.005 |

TABLE 1-continued

|  | Example 1 | Example 5 | Comparative Example 1 | Comparative Example 2 |
|---|---|---|---|---|
| Coefficient of Variation* (%) | 0.07 | 0.26 | 0.25 | 0.38 |

Note:

$$\text{*Coefficient of Variation (\%)} = \frac{\sqrt{\dfrac{\sum\limits_{i=1}^{n}(x_i - \bar{x})^2}{n-1}}}{\bar{x}} \times 100$$

$\bar{x}$: averaged value
$x_i$: ith measured value
n: time of measurement (hereinafter the same)

TABLE 2

|  | Example 5 | Comparative Example 2 |
|---|---|---|
| Measured Value for 0.63 mg of water (μg) | 614 | 603 |
|  | 613 | 606 |
|  | 617 | 591 |
|  | 612 | 617 |
|  | 615 | 600 |
| Averaged Value (μg) | 614 | 603 |
| Coefficient of Variation (%) | 0.31 | 1.7 |

In the titration curve of Comparative Example 1 (FIG. 2), point E indicates that the measurement is supposed to come to an end. However, it is assumed from the disordered titration curve after point E that adsorbed water enters into titration vessel (2) while repeating adsorption and desorption. When electrolytic solution (18) was made to flow backward into blowing tube (3), at the points indicated by arrows, so that oil droplets or solid substances deposited onto the inner wall of the blowing tube might be dissolved out, the corresponding signals appeared. It is obvious from this fact that part of the water had been adsorbed by the oil droplets or solid substances.

To the contrary, the titration curve of Example 1 (FIG. 3) shows very little disorder, and no signal appears even when electrolytic solution (18) is made to flow backward into blowing tube (3) for washing the inner wall of the tube. It can be seen, therefore, that no water had been adsorbed onto the inner wall of the blowing tube. Further, it can be seen, by comparing the results of Example 1 and those of Comparative Example 1, that the measurement method according to the present invention improves precision and shortens the measurement time because of the minimized tailing.

COMPARATIVE EXAMPLE 3

The procedure of Example 1 was repeated except for using 200 ml of an electrolytic solution prepared by dissolving 14.8 g of 4-dimethylaminopyridine, 11.8 g of 1,3-di-(2-pyridyl)propane, 7.6 g of sulfur dioxide, 5 g of iodine and 50 ml of ethylene glycol monomethyl ether in chloroform. The results obtained are shown in Table 3 below.

TABLE 3

| Measured Value for 10.0 mg of Water (mg) | 9.900 |
|---|---|
|  | 9.898 |
|  | 9.862 |
|  | 9.888 |
| Averaged Value (mg) | 9.887 |
| Coefficient of | 0.18 |

TABLE 3-continued

Variation (%)

The titration curve obtained showed disorder after point E similarly to Comparative Example 1.

COMPARATIVE EXAMPLE 4

The procedure of Example 1 was repeated except for using 30 ml of ethanol in place of ethylene glycol. As a result, the titration curve showed disorder even after point E similarly to Comparative Example 1.

COMPARATIVE EXAMPLE 5

The procedure of Example 1 was repeated except for using propylene glycol in place of methanol. In this case, measurement of the water content of a sample could not be carried out since a KF reaction did not proceed normally.

As described above, the electrolytic solution for KF coulometric titration in accordance with the present invention is advantageous for the measurement of the water content of solid samples by the use of a water vaporization apparatus. It is particularly suitable for the measurement of trace amounts of water. According to the water content measurement method using the electrolytic solution of the invention, the precision of measurement can be heightened, and the measurement time required can be reduced.

While the invention has been described in detail and with reference to specific embodiments thereof, it will be apparent to one skilled in the art that various changes and modifications can be made therein without departing from the spirit and scope thereof.

What is claimed is:

1. A method for measuring the water content of a solid substance comprising the following steps:

heating a solid substance to vaporize any water therein;

contacting any water vapor formed in the heating step with an electrolytic solution for Karl Fischer's coulometric titration, wherein the electrolytic solution consists essentially of:

(1) 0.1 to 3 percent by weight, calculated as free iodine, of an iodide or iodine;

(2) sulfur dioxide;

(3) an amine selected from the group consisting of pyridine derivatives, imidazole, and imidazole derivatives; and (4) a solvent which is a mixture of (a) from 3 to 30 percent by volume, based on the electrolytic solution, of a polyhydric alcohol or an ether compound thereof, (b) methanol, and (c) a halogenated hydrocarbon or an aromatic hydrocarbon; and measuring the water content of the electrolytic solution by Karl Fischer's coulometric titration.

2. The method of claim 1 wherein the volumetric ratio of polyhydric alcohol or an ether compound thereof to methanol in the electrolytic solution is 1:0.1 to 1:15.

3. The method of claim 1 wherein the volumetric ratio of polyhydric alcohol or an ether compound thereof to methanol in the electrolytic solution is 1:1 to 1:8.

4. The method of claim 1 wherein component (a) of said solvent is a polyhydric alcohol having 2 to 4 carbon atoms and 2 or 3 hydroxy groups.

* * * * *